(12) United States Patent
Moon et al.

(10) Patent No.: US 9,116,140 B2
(45) Date of Patent: Aug. 25, 2015

(54) APPARATUS AND METHOD FOR NON-DESTRUCTIVELY DIAGNOSING CROP GROWTH USING TERAHERTZ WAVES

(71) Applicant: ELECTRONICS AND TELECOMMUNICATIONS RESEARCH INSTITUTE, Daejeon-si (KR)

(72) Inventors: Ae-Kyeung Moon, Daegu-si (KR); Kyu-Hyung Kim, Daegu-si (KR)

(73) Assignee: ELECTRONICS AND TELECOMMUNICATIONS RESEARCH INSTITUTE, Daejeon-si (KR)

( * ) Notice: Subject to any disclaimer, the term of this patent is extended or adjusted under 35 U.S.C. 154(b) by 170 days.

(21) Appl. No.: 13/845,891

(22) Filed: Mar. 18, 2013

(65) Prior Publication Data

US 2014/0064568 A1 Mar. 6, 2014

(30) Foreign Application Priority Data

Sep. 3, 2012 (KR) .......................... 10-2012-0097348

(51) Int. Cl.
*G06K 9/00* (2006.01)
*G01N 33/00* (2006.01)
*G01N 21/3581* (2014.01)

(52) U.S. Cl.
CPC ........ *G01N 33/0098* (2013.01); *G01N 21/3581* (2013.01)

(58) Field of Classification Search
CPC combination set(s) only.
See application file for complete search history.

(56) References Cited

U.S. PATENT DOCUMENTS

| 5,130,545 | A | * | 7/1992 | Lussier ....................... 250/458.1 |
| 5,981,958 | A | * | 11/1999 | Li et al. ....................... 250/459.1 |
| 6,385,544 | B1 | * | 5/2002 | Mafra-Neto ....................... 702/5 |
| 6,573,512 | B1 | * | 6/2003 | Lucia et al. ................. 250/458.1 |
| 6,597,991 | B1 | * | 7/2003 | Meron et al. ....................... 702/3 |
| 2003/0069697 | A1 | * | 4/2003 | Mafra-Neto et al. ............. 702/2 |
| 2004/0115755 | A1 | * | 6/2004 | Croy et al. ....................... 435/25 |
| 2005/0098713 | A1 | * | 5/2005 | Holland ......................... 250/221 |
| 2007/0013908 | A1 | * | 1/2007 | Lee et al. ....................... 356/301 |
| 2010/0039804 | A1 | * | 2/2010 | Budde et al. .................... 362/231 |
| 2010/0145624 | A1 | * | 6/2010 | Kishore et al. .................. 702/19 |
| 2011/0041399 | A1 | * | 2/2011 | Stachon et al. .......... 47/58.1 LS |
| 2011/0097771 | A1 | * | 4/2011 | Emmanuel et al. ........... 435/134 |
| 2011/0153053 | A1 | * | 6/2011 | Kim et al. ...................... 700/103 |
| 2012/0109614 | A1 | * | 5/2012 | Lindores ......................... 703/11 |

FOREIGN PATENT DOCUMENTS

KR 1020090098458 A 9/2009
KR 1020110091060 A 8/2011

OTHER PUBLICATIONS

Hadjiloucas. "Measurements of Leaf Water Content Using Terahertz Radiation" Feb. 1999, IEEE.*

* cited by examiner

*Primary Examiner* — Alex Liew
(74) *Attorney, Agent, or Firm* — Ladas & Parry LLP

(57) ABSTRACT

An apparatus and method for non-destructively diagnosing crop growth using terahertz waves are provided. The apparatus includes an information extractor configured to extract status information on a crop from information on an image of the crop taken using terahertz waves, a database configured to store growth-stage-specific information on the crop, and a status determiner configured to compare the status information on the crop extracted by the information extractor with the growth-stage-specific information stored in the database, and determine the degree of growth of the crop.

10 Claims, 3 Drawing Sheets

WATER CONTENT

APPARATUS AND METHOD FOR NON-DESTRUCTIVELY DIAGNOSING CROP GROWTH USING TERAHERTZ WAVES

CROSS-REFERENCE TO RELATED APPLICATION

This application claims the benefit under 35 U.S.C. §119 (a) of a Korean Patent Application No. 10-2012-0097348, filed on Sep. 3, 2012, the entire disclosure of which is incorporated herein by reference for all purposes.

BACKGROUND

1. Field

The following description relates to technology for automating diagnoses of crop growth, and more particularly, to an apparatus and method for non-destructively diagnosing crop growth using terahertz waves.

2. Description of the Related Art

The word "terahertz" is a combination of the prefix "tera" meaning a value obtained by raising 10 to the power of 12, and a unit of frequency "hertz." Terahertz waves denote electromagnetic waves having frequencies of 0.1 to 10 THz, that is, wavelengths of 30 μm to 3 mm, in the electromagnetic wave spectrum. Thus, a terahertz wave is an electric wave having the shortest wavelength and is also a light wave having the longest wavelength. Technology employing such terahertz waves has not yet been exploited because an appropriate signal source or a detection technique has not been developed. However, due to recent remarkable advancement in scientific technology, various techniques are being introduced, and terahertz waves are being recognized as an important tool in future scientific technology fields. Terahertz waves have both the transmissivity of electromagnetic waves and the directivity of light waves. Thus, it is possible to obtain a transmission image, such as an X-ray image, using terahertz waves, and also to analyze unique physical properties of a material from the terahertz region of a spectrum. For this reason, terahertz waves are also referred to as T-rays.

Since terahertz waves have superior transmissivity to existing X-ray imaging or magnetic resonance imaging (MRI), and can transmit a large amount of information several thousand times that of existing mobile communication, research is under way to apply terahertz wave technology to a variety of fields, such as histopathological diagnosis and molecular research. Since terahertz waves as a source for imaging have sufficiently short wavelengths compared to traditional microwaves, terahertz waves have excellent spatial resolution and can pass through most objects except water and metal. Also, due to a lower frequency than X-rays, it is possible to obtain a high-resolution image without damaging the skin tissue of a person.

Meanwhile, to harvest crops, for example, to automatically harvest oriental melons, it is necessary to select properly ripened oriental melons. When oriental melons are covered by leaves, it is necessary to find how ripe the oriental melons are by drawing the leaves aside and taking images of the oriental melons. Currently, the operation of drawing leaves is manually performed. When the operation is automated, it lacks reliability because it is necessary to draw a large number of leaves. Also, in comparison with a case in which a person manually performs the operation, crops suffer greater damage.

SUMMARY

The following description relates to non-destructively diagnosing crop growth using terahertz waves, and also to preventing disease and insect pests of crops according to the diagnosis.

In one general aspect, an apparatus for non-destructively diagnosing crop growth using terahertz waves includes: an information extractor configured to extract status information on a crop from information on an image of the crop taken using terahertz waves; a database configured to store growth-stage-specific information on the crop; and a status determiner configured to compare the status information on the crop extracted by the information extractor with the growth-stage-specific information stored in the database, and determine the degree of growth of the crop.

Here, the information extractor may extract water content of the crop and property information on the crop from the information on the image of the crop taken using the terahertz waves.

Here, the status determiner may compare the water content of the crop and the property information on the crop extracted by the information extractor with the growth-stage-specific information on the crop stored in the database, and determine whether there are disease and insect pests, and nutritional status of the crop.

In addition, the status determiner may compare the water content of the crop and the property information on the crop extracted by the information extractor with growth-stage-specific property information on a fruit stored in the database, and determine whether or not there is fruit.

In another general aspect, a method of non-destructively diagnosing crop growth using terahertz waves includes: an information extraction operation of extracting status information on a crop from information on an image of the crop taken using terahertz waves; and a status determination operation of comparing the extracted status information on the crop with previously stored growth-stage-specific information on the crop, and determining the degree of growth of the crop.

Other features and aspects will be apparent from the following detailed description, the drawings, and the claims.

Figure 1:
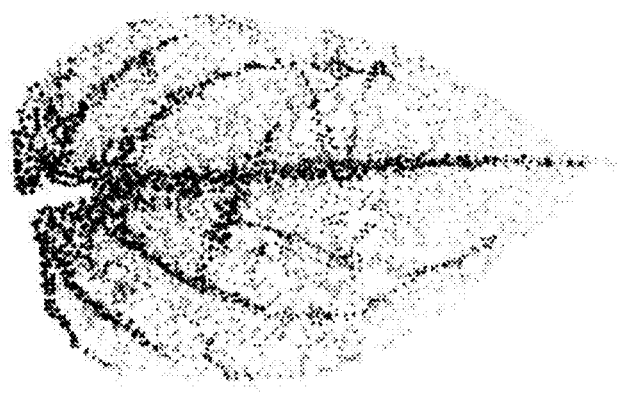
FIG. 1 is a two-dimensional (2D) image taken using terahertz waves.
Figure 1:
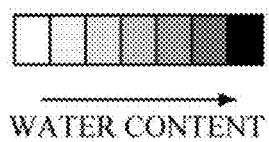

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

Combinations of respective blocks in an accompanying block diagram and respective operations in a flowchart may be performed by computer program instructions. These computer program instructions can be mounted on a processor of a general purpose computer, a special purpose computer, or other programmable data processing equipment, and thus the instructions performed by the processor of the computer or other programmable data processing equipment generate a means for performing functions described in the respective blocks of the block diagram or the respective operations of the flowchart. To implement functions in a specific way, these computer program instructions can be stored in a computer-usable or computer-readable memory capable of aiming for a computer or other programmable data processing equipment, so that the instructions stored in the computer-usable or computer-readable memory can also produce a manufactured item including an instruction means for performing functions described in the respective blocks of the block diagram or the respective operations of the flowchart.

In addition, each block or operation may indicate a part of a module, a segment or a code including one or more executable instructions for executing specific logical function(s). It should be noted that mentioned functions described in blocks or operations can be executed out of order in some alternative embodiments. For example, two consecutively shown blocks or operations can be performed substantially at the same time, or can be performed in a reverse order according to the corresponding functions.

FIG. 1 is a two-dimensional (2D) image taken using terahertz waves. Since terahertz waves are strongly absorbed by moisture, it is possible to easily observe a change in biological tissue or cells according to water content. As shown in the drawing, transmissivity of terahertz waves differs according to water content. In a leaf vein with high water content, the amount of absorbed terahertz waves is greater than the amount of passing terahertz waves, and thus the leaf vein is shown dark. On the other hand, in a leaf body with low water content, the amount of passing terahertz waves is greater than the amount of absorbed terahertz waves, and thus the leaf body is shown bright.

Figure 2:
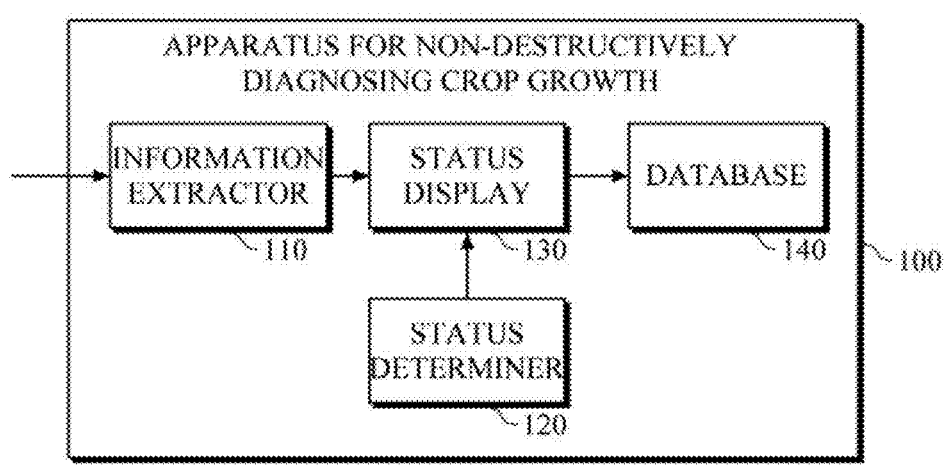
FIG. 2 is a block diagram of an apparatus for non-destructively diagnosing crop growth using terahertz waves according to an embodiment of the present invention.

FIG. 2 is a block diagram of an apparatus for non-destructively diagnosing crop growth using terahertz waves according to an embodiment of the present invention.

Prior to description of FIG. 2, although not shown in the drawing, a terahertz camera can be used to acquire an image of a crop using terahertz waves. Here, a user may manually take the image using the terahertz camera, or may take the image in connection with an automation system. The image of the crop taken in this way is transmitted to an apparatus 100 for non-destructively diagnosing crop growth using terahertz waves.

Referring to FIG. 2, the apparatus 100 for non-destructively diagnosing crop growth using terahertz waves may include an information extractor 110, a database 120, a status determiner 130, and a status display 140.

The information extractor 110 may extract status information on a crop from information on an image of the crop taken using terahertz waves. For example, an image generated using terahertz waves is shown differently according to water content, and thus it is possible to determine water content of a crop. In a leaf containing a lot of water, a leaf vein is clearly distinguished from a leaf body according to water content, but in a leaf containing little water over time, a leaf vein is dimly shown. If all water contained in a leaf comes out, it is not possible to see the shape of the leaf. Also, property information (e.g., a value of carbohydrate according to photosynthesis) the crop may be extracted by analyzing an absorption spectrum, reflection spectrum or transmission spectrum of terahertz waves included in the information on the image of the crop taken using terahertz waves.

The database 120 stores growth-stage-specific information on the crop. Here, the growth-stage-specific information may be growth-stage-specific property information (e.g., a change in the value of carbohydrate according to the degree of photosynthesis) on the crop, property information on leaf veins according to growth status, information on growth-stage-specific spectrums (absorption, reflection, transmission, etc. spectrum of terahertz waves), property information according to leaf vein transmission, growth-stage-specific property information on a fruit, and so on.

The status determiner 130 may determine the degree of growth of the crop by comparing the status information on the crop extracted by the information extractor 110 with the growth-stage-specific information stored in the database 120. Also, the status determiner 130 may determine status of the crop such as whether or not there are disease and insect pests in the crop, and nutritional status by comparing the water content of the crop and the property information on the crop with the growth-stage-specific information on the crop stored in the database 120.

In addition, the status determiner 130 may determine whether or not the crop is bearing fruit. Since terahertz waves have high spatial resolution of light waves, transmissivity of electric waves, and safety for biological tissue, it is possible to photograph a fruit of the crop covered by leaves without destroying biological tissue. In this case, information on a fruit is also included in the property information and the water content information on the crop extracted by the information extractor 110, and may be compared with growth-stage-specific property information on the crop stored in the database 120 to determine whether or not there is fruit.

The status display 140 may display the status of the crop, such as whether or not there is a fruit, the degree of growth of the crop, or whether there are disease and insect pests, and the nutritional status, determined by the status determiner 130, on a liquid crystal display (LCD) panel. In this case, the LCD panel is merely one of methods for the status display 140 to display status of the crop, etc., and the present invention is not limited to the LCD panel. For example, when the crop has a fruit, and the degree of growth of the crop corresponds to harvest time, these may be displayed, and when it is determined that there are disease and insect pests based on disease and pest diagnosis results, this may be displayed for disease and insect pest control. In addition, the nutritional status (e.g., a lack of water) of the crop may be displayed, and the user may be notified of the nutritional status.

Figure 3:
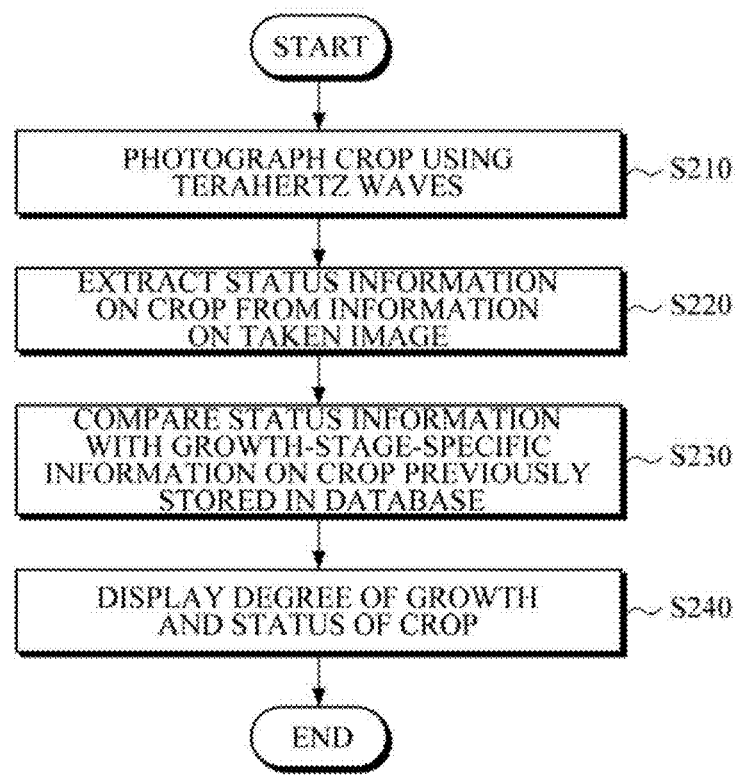
FIG. 3 is a flowchart illustrating a method of non-destructively diagnosing crop growth using terahertz waves according to another embodiment of the present invention.

FIG. 3 is a flowchart illustrating a method of non-destructively diagnosing crop growth using terahertz waves according to another embodiment of the present invention.

First, a crop is photographed using terahertz waves (operation 210). For example, using a terahertz camera, the crop may be photographed. At this time, an automation system may be used to photograph the crop, or a user may manually photograph the crop.

Subsequently, status information on the crop is extracted from information on the taken image (operation 220). For example, an image generated using terahertz waves is shown differently according to water content, and thus it is possible to determine water content of a crop. In a leaf containing a lot of water, a leaf vein is clearly distinguished from a leaf body according to water content, but in a leaf containing little water over time, a leaf vein is dimly shown. Also, property information (e.g., a value of carbohydrate according to photosynthesis), etc. on the crop may be extracted from an absorption spectrum, reflection spectrum or transmission spectrum of terahertz waves.

The status information on the crop extracted from the information on the taken image is compared with growth-stage-specific information on the crop previously stored in the database 120 to determine whether or not there is fruit, the degree of growth of the crop, and status of the crop such as whether or not there are disease and insect pests in the crop, and nutritional status (operation 230).

Subsequently, the determined degree of growth of the crop and the determined status of the crop are displayed (operation 240). In this case, when the degree of growth of the crop corresponds to harvest time, this may be displayed, and when it is determined that there are disease and insect pests based on disease and pest diagnosis results, this may be displayed for disease and insect pest control. In addition, the nutritional status (e.g., a lack of water) of the crop may be displayed, and the user may be notified of the nutritional status.

An apparatus and method for non-destructively diagnosing crop growth using terahertz waves according to an embodiment of the present invention can non-destructively diagnose crop growth using terahertz waves, and also prevent disease and insect pests of a crop according to the diagnosis.

The present invention can be implemented as computer readable codes in computer readable record media. Computer readable record media include all types of record media in which computer readable data is stored. Examples of computer readable record media include a ROM, a RAM, a CD-ROM, a magnetic tape, a floppy disk, and optical data storage. Further, the record medium may be implemented in the form of a carrier wave such as Internet transmission. In addition, the computer readable record medium may be distributed to computer systems over a network, in which computer readable codes may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for non-destructively diagnosing crop growth using terahertz waves, comprising:
    an information extractor configured to extract status information on a crop from information on an image of the crop taken using terahertz waves;
    a database configured to store growth-stage-specific information on the crop; and
    a status determiner configured to compare the status information on the crop extracted by the information extractor with the growth-stage-specific information stored in the database, and determine a degree of growth of the crop;
    wherein the information extractor extracts water content of the crop and property information on the crop from the information on the image of the crop taken using the terahertz waves; and
    wherein the status determiner compares the water content of the crop and the property information on the crop extracted by the information extractor with the growth-stage-specific information on the crop stored in the database, and determines whether there are disease and insect pests, and nutritional status of the crop.

2. An apparatus for non-destructively diagnosing crop growth using terahertz waves, comprising:
    an information extractor configured to extract status information on a crop from information on an image of the crop taken using terahertz waves;
    a database configured to store growth-stage-specific information on the crop; and
    a status determiner configured to compare the status information on the crop extracted by the information extractor with the growth-stage-specific information stored in the database, and determine a degree of growth of the crop;
    wherein the information extractor extracts water content of the crop and property information on the crop from the information on the image of the crop taken using the terahertz waves; and
    wherein the status determiner compares the water content of the crop and the property information on the crop extracted by the information extractor with growth-stage-specific property information on a fruit stored in the database, and determines whether or not the crop is bearing fruit.

3. A method of non-destructively diagnosing crop growth using terahertz waves, comprising:
    an information extraction operation of extracting status information on a crop from information on an image of the crop taken using terahertz waves; and
    a status determination operation of comparing the extracted status information on the crop with previously stored growth-stage-specific information on the crop, and determining a degree of growth of the crop;
    wherein the information extraction operation includes extracting water content of the crop and property information on the crop from the information on the image of the crop taken using the terahertz waves; and
    wherein the status determination operation includes comparing the water content of the crop and the property information on the crop extracted in the information extraction operation with the previously stored growth-stage-specific information on the crop, and determining whether there are disease and insect pests, and nutritional status of the crop.

4. A method of non-destructively diagnosing crop growth using terahertz waves, comprising:
    an information extraction operation of extracting status information on a crop from information on an image of the crop taken using terahertz waves; and
    a status determination operation of comparing the extracted status information on the crop with previously stored growth-stage-specific information on the crop, and determining a degree of growth of the crop;
    wherein the information extraction operation includes extracting water content of the crop and property information on the crop from the information on the image of the crop taken using the terahertz waves; and
    wherein the status determination operation further includes comparing the water content of the crop and the property information on the crop extracted in the information extraction operation with previously stored property information on a fruit according to growth stages of the crop, and determining whether or not there is fruit.

5. The apparatus of claim 1, wherein further comprising a display configured to display the degree of growth of the crop determined by the status determiner.

6. The apparatus of claim 2, wherein further comprising a display configured to display the degree of growth of the crop determined by the status determiner.

7. The method of claim 3, further comprising a status display operation of displaying the degree of growth of the crop determined in the status determination operation.

8. The method of claim 4, further comprising a status display operation of displaying the degree of growth of the crop determined in the status determination operation.

9. The apparatus of claim 1 wherein the property information is extracted by analyzing an absorption spectrum, a reflection spectrum, or a transmission spectrum of terahertz waves.

10. An apparatus for non-destructively diagnosing crop growth using terahertz waves, comprising:
- an information extractor configured to extract status information on a crop from information on an image of the crop taken using terahertz waves;
- a database configured to store growth-stage-specific information on the crop; and
- a status determiner;
- wherein the information extractor extracts water content of the crop and property information on the crop from the information on the image of the crop taken using the terahertz waves; and
- a status determiner configured to compare the water content of the crop and the property information on the crop extracted by the information extractor with the growth-stage-specific information on the crop stored in the database.

* * * * *